United States Patent [19]

Wilson et al.

[11] Patent Number: 4,808,403
[45] Date of Patent: Feb. 28, 1989

[54] USE OF N,N-DIETHYL-M-TOLUAMIDE AND/OR THE ETHYL ESTER OF 2-METHYL-3-PENTENOIC ACID AS INSECT ATTRACTANTS

[75] Inventors: Richard A. Wilson, Westfield, N.J.; Jerry F. Butler, Gainesville, Fla.; Donald Withycombe, Lincroft, N.J.; Braja D. Mookherjee, Holmdel, N.J.; Ira Katz, West Long Branch, N.J.; Kenneth R. Schrankel, Tinton Falls, N.J.

[73] Assignees: International Flavors & Fragrances Inc., New York, N.Y.; The University of Florida, Gainesville, Fla.

[21] Appl. No.: 26,979

[22] Filed: Mar. 17, 1987

[51] Int. Cl.[4] ............................................. A01N 25/00
[52] U.S. Cl. ................................................... 424/84
[58] Field of Search ...................................... 424/84

[56] References Cited

FOREIGN PATENT DOCUMENTS 0103841  6/1982  Japan .................................... 424/84

OTHER PUBLICATIONS

Agricultural Handbook No. 239 published by the Agricultural Research Service of the U.S. of America Dept. of Agriculture, issued Jun. 1963, entitled: "Material Tested as Insect Attractants", M. Beroza and N. Green, cover page and pp. 1–8 and p. 31; p. 85 and p. 99 showing the attractancy of Item 4082.

Neumark, Jacobson and Teich, Environmental Letters 7(1), 21–30 (1974) title: "Field Evaluation of Propylure, Hexalure, and their Formulations with DEET, Dodecyl Acetate, and an Antioxidant as Attractants for Male Pink Bollworm Moths" (and abstr. at Chem. Abstrs., vol. 81, 1974, Abstract No. 146849c).

Jones and Jacobson, Science, vol. 159, Jan. 5, 1968, pp. 99 and 100, title: "Isolation of N,N–Diethyl-m-Toluamide (DEET) from Female Pink Bollworm Moths".

Primary Examiner—Albert T. Meyers
Assistant Examiner—John M. Kilwyne
Attorney, Agent, or Firm—Arthur L. Liberman

[57] ABSTRACT

Described are the N,N-diethyl-m-toluamide having the structure:

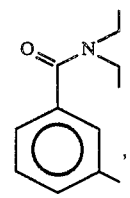

and the ethyl ester of 2-methyl-3-pentenoic acid having the structure:

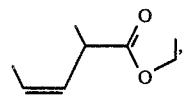

taken alone or taken in combination as attractants for house flies (*Musca domestica* L. (Diptera:Muscidae)). The N,N-diethyl-m-toluamide and ethyl ester of 2-methyl-3-pentenoic acid taken alone or in combination find utility primarily as bait enhancers for acute toxins and/or trapping devices.

1 Claim, 6 Drawing Sheets

FIG.I

FIG.2
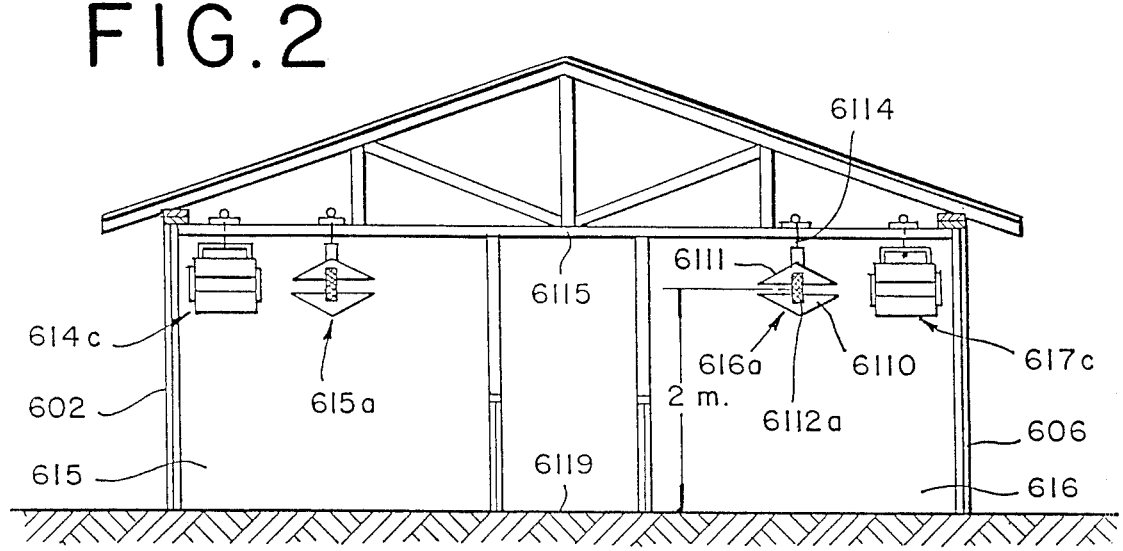
FIG.3
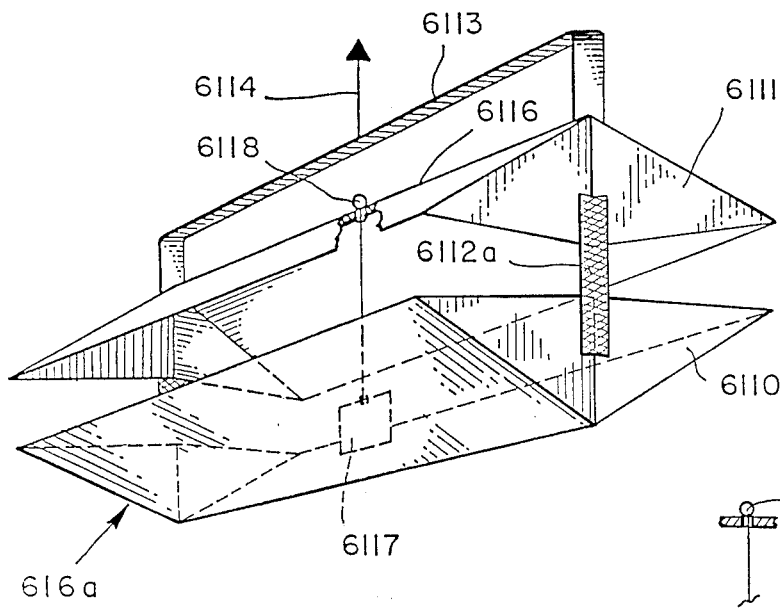
FIG.4

USE OF N,N-DIETHYL-M-TOLUAMIDE AND/OR THE ETHYL ESTER OF 2-METHYL-3-PENTENOIC ACID AS INSECT ATTRACTANTS

BACKGROUND OF THE INVENTION

This invention relates to insect attractants for house flies (*Musca domestica* L.(Diptera:Muscidae)). More particularly this invention relates to compositions of matter containing N,N-diethyl-m-toluamide and/or the ethyl ester of 2-methyl-3-pentenoic acid as attractants for *Musca domestica* L.(Diptera:Muscidae).

Fast intercontinental travel and trade are stepping up changes of importing nonindigenous insect pests into the United States. Attractants, or lures, can be of considerable aid in facilitating the early detection of such insect pests, and they are of vital importance in measuring the progress of a program aimed at eradicating a species that has become established.

In Agriculture Handbook No. 239 published by the Agricultural Research Service of the United States of America Department of Agriculture issued in June 1963 entitled, "Materials Tested As Insect Attractants", compiled by M. Beroza and N. Green, N,N-diethyl-m-toluamide having the structure:

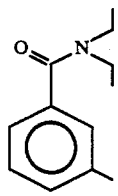

is indicated to have low attractancy indeces ("1" on a scale of 1 to 3) for Drosophila and the European chafer; and a moderate attractancy index ("2" on a scale of 1 to 3) for the Pink Bollworm.

In Beroza, et al, the compound N,N-dibuty-m-toluamide having the structure:

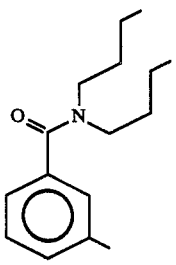

has low attractancy indeces ("1" on a scalen of 1 to 3) for the Oriental Fruit Fly, the Mediterranean Fruit Fly, the Mexican Fruit Fly, the Gypsy Moth and the Bollweevil as well as the house fly (*Musca domestic* L.). It is indicated to have a moderate attractancy index ("2" on a scale of 1 to 3) for the Pink Bollworm.

The compound N,N-dibutyl-o-toluamide is indicated to have low attractancy indeces ("1" on a scale of 1 to 3) for the Oriental Fruit Fly, the Melon Fly, the Mediterranean Fruit Fly, the Mexican Fruit Fly, the Bollweevil and the house fly (*Musca domestic* L.). N,N-dibutyl-o-toluamide has the structure:

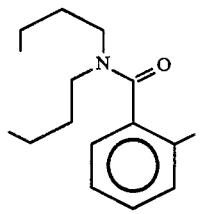

The compound N,N-diisoporpyl-o-toluamide having the structure:

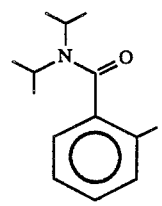

is indicated to have low attractancy indeces ("1" on a scale of 1 to 3) for the Oriental Fruit Fly, the Melon Fly, the Mediterranean Fruit Fly, the Mexican Fruit Fly, the Pink Bollworm, the Bollweevil and the house fly (*Musca domestica* L.).

The compound N,N-dibutyl-p-toluamide having the structure:

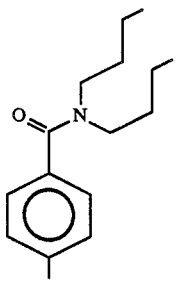

is indicated to have low attractancy indeces ("1" on a scale of 1 to 3) for the Oriental Fruit Fly, the Mediterranean Fruit Fly, the Mexican Fruit Fly, the Gypsy Moth, the Bollweevil and the house fly (*Musca domestica* L.).

The compound having the structure:

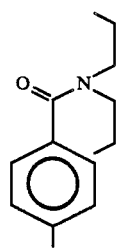

which is N,N-dipropyl-p-toluamide is indicated to have low attractancy indeces ("1" on a scale of 1 to 3) for the Oriental Fruit Fly, the Mediterranean Fruit Fly, the Mexican Fruit Fly and the house fly (*Musca domestica* L.).

The ethyl ester of crotonic acid is indicated to have moderate attractancy indeces ("2" on a scale of 1 to 3)

for the Oriental Fruit Fly, the Melon Fly and the Mediterranean Fruit Fly and low attractancy indeces ("1" on a scale of 1 to 3) for the Mexican Fruit Fly and the Gypsy Moth.

Nothing in the prior art discloses the use of N,N-diethyl-m-toluamide or the ethyl ester of 2-ethyl-3-pentenoic acid taken alone or in combination in attracting certain species of insects including *Musca domestica L.*(Diptera:Muscidae) at a high level; higher than standard Commercial Products, e.g., GOLDEN MALRIN ® or equivalent to standard Commercial Products, e.g., GOLDEN MALRIN ®.

BRIEF DESCRIPTION OF THE DRAWINGS

FIG. 2 is a cut-away side elevation view (schematic) indicating the positioning of sticky traps in a test barn taken along lines 2—2 of FIG. 1.

FIG. 3 is a perspective schematic view of a test sticky trap showing the positioning of the slow release material suspended inside of the trap structure.

FIG. 4 is a cut-away section in perspective of the sticky trap system of FIG. 3.

SUMMARY OF THE INVENTION

Figure 1:
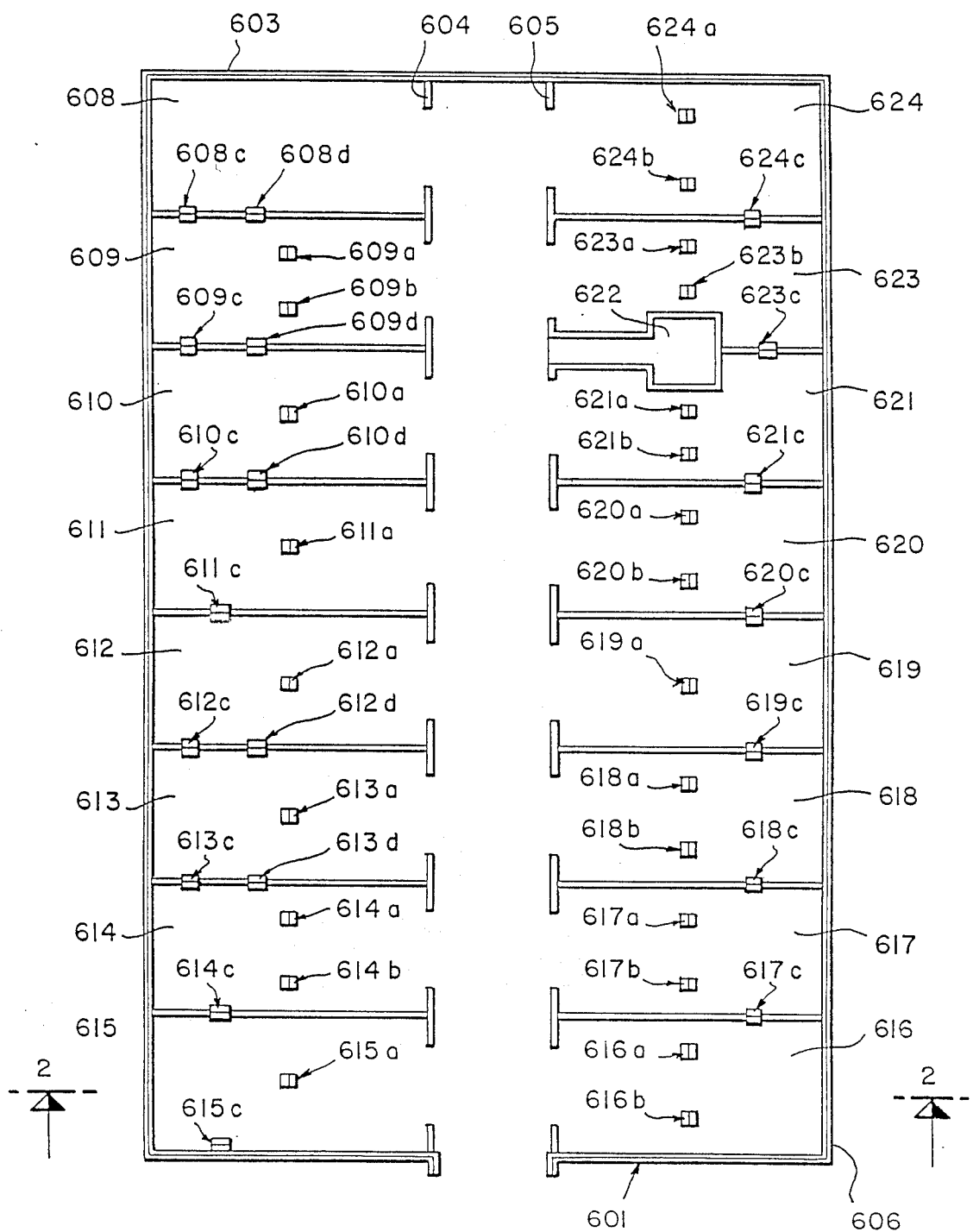
FIG. 1 is a schematic top view of the location of insect traps containing formulated slow release insect attractants and control materials (known attractant, GOLDEN MALRIN ® fly bait).

Our invention relates to the use of N,N-diethyl-m-toluamide having the structure:

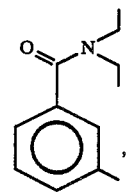

the ethyl ester of ester of 2-methyl-3-pentenoic acid having the structure:

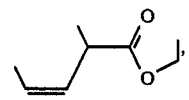

mixtures therof, and mixtures of N,N-diethyl-m-toluamide having the structure:

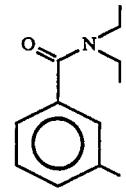

and dimethyl disulfide having the structure:

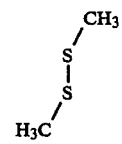

as attractants for house flies (*Musca domestica L.*(Diptera:Muscidae)).

A trapping system which is the basis of a first testing technique used in testing the efficacy of the N,N-diethyl-m-toluamide, the ethyl ester of 2-methyl-3-pentenoic acid, mixtures of same and mixtures of N,N-diethyl-m-toluamide and dimethyl disulfide is a standard ZOECON ® sticky trap consisting of a ZOECON PHEROCON ® 1C trap with a 2 cm×2 cm strip of formulated slow release attractant suspended on a paper clip inside the trap. The traps are placed in a goat barn and are suspended from the rafters. Trap placement was replicated in the four quadrants of the barn. Traps were placed in the barn for seven days and the insects collected were identified and counted. Evidence of insects visiting the traps were also counted as insect specks inside or outside the traps. All test materials were compared with a standardized check treatment consisting of 0.5 grams of GOLDEN MALRIN ® fly bait inside of the flow release packet hung like the other compounds.

Our invention also relates to the formation of insect attractant-containing polymeric pellets by means of introduction into a single screw or twin screw extruder of, in series, thermoplastic polymer followed by insect attractant which is compatible with the thermoplastic polymer, in turn, followed by introduction of a gaseous blowing agent or blowing agent which will produce a gas which is inert to the polymer and to the insect attractant, e.g., N,N-diethyl-m-toluamide, the ethyl ester of 2-methyl-3-pentenoic acid, mixtures of same, and mixtures of N,N-diethyl-m-toluamide and dimethyl disulfide.

In the alternative, the use of the foaming agent can be omitted.

The nature of the extruder utilized in this aspect of our invention to form the polymeric insect attractant particles of our invention may be either single screw or double screw. Thus, the types of extruder that can be used are disclosed at pages 246–267 and 332–349 of the Modern Plastics Encyclopedia, 1982–1983 published by the McGraw-Hill Publishing Company, the disclosure of which is incorporated by reference herein. More specifically, examples of extruders which are useable in carrying out this aspect of our invention (with modification for introduction of insect attractant downstream from introduction of the polymer and optionally with a further modification that the gaseous blowing agent is introduced still further downstream from the point of introduction of insect attractant) are as follows:

1. The Welex "Super Twinch" 3.5" extruder manufactured by Welex Incorporated, 850 Jolly Road, Blue Bell, Pa. 19422;
2. Krauss-Maffei twin screw extruder manufactured by the Krauss-Maffei Corporation/Extruder Division, 3629 West 30th Street South, Wichita, Kans. 67277;
3. Modified Sterling Model 4000 and 5000 series extruder manufactured by Sterling Extruder Corporation of 901 Durham Avenue, South Plainfield, N.J.;
4. CRT ("Counter-Rotating Tangential⇌") Twin Screw Extruder manufactured by Welding Engineers, Inc. of King of Prussia, Pa. 19406;
5. The Leistritz Twin Screw Dispersion Compounder manufactured by the American Leistritz Extruder Corporation of 198 U.S. Route 206 South, Somerville, N.J. 08876;
6. The ZSK Twin Screw Co-Rotating Extruder manufactured by the Werner & Pfleiderer Corporation of 663 East Crescent Avenue, Ramsey, N.J. 07446;
7. The Farrel Extruder manufactured by Farrel Connecticut Division, Emhart Machinery Group, Ansonia, Conn. 06401;
8. The MPC/V Baker Perkins Twin Screw Extruder manufactured by the Baker Perkins Inc. Chemical Machinery Division of Saginaw, Mich. 48601; and
9. The Berstorff Single Screw, Twin Screw, or Foam Extrusion Equipment manufactured by Berstorff Corporation, P.O. Box 240357, 8200-A Arrowridge Boulevard, Charlotte, N.C. 28224.

In producing the insect attractant-containing polymer particles of our invention, various polymers may be utilized, for example, low density polyethylene, high density polyethylene, polypropylene, the co-polymer of ethylene and vinyl acetate, and polyvinyl chloride. More specifically, the polymers used in the practice of our invention may be co-polymers of ethylene and a polar vinyl monomer selected from (a) vinyl acetate; (b) ethyl acrylate; (c) methyl acrylate; (d) butyl acrylate and (e) acrylic acid including the hydrolyzed co-polymer of ethylene and vinyl acetate. Preferred co-polymers are ethylene vinyl acetate with about 9 to 60% vinyl acetate and ethylene/ethyl acrylate with about 6 to 18% ethyl acrylate.

Resins of the type disclosed for use as co-polymers are commercially available in the molding powder form. For example, ethylene vinyl acetate co-polymers are marketed by the E. I. duPont de Nemours Company under the tradename "ELVAX ®" and by the Arco Polymer Division under the trademark "DYLAND" ® and by the Exxon Corporation of Linden, N.J. under the trademark "DEXXON" ®. Ethylene/ethyl acrylate co-polymers are marketed by Union Carbide Corporation under the tradename "EEA Resins" ®.

The polymer is added to the single screw or twin screw extruder at a feed rate in the range of from about 80 up to about 300 pounds per hour while maintaining the temperature in the screw extruder between about 160° and about 240° C. If the polymer or co-polymer powder is added to the extruder at a reference "barrel segment", then the insect attractant is added to the extruder under pressure downstream from the addition point of the polymer at 1 or more "barrel segments" S-2, S-3, S-4, S-5, S-6, S-7, S-8 or S-9.

Thus, the invention provides a process for forming insect attractant-containing polymeric particles such as polymeric pellets which include a relatively high concentration of insect attractants. The insect attractant added at "barrel segments" "S-2, S-3, S-4, S-5, S-6, S-7, S-8 or S-9 of the single screw or twin screw extruder is to be compatible with the polymer added at "barrel segment" S-1 of the single screw or twin screw extruder.

The proportion of insect attractant is limited only by either (a) its solubility in the resin or mixture of resins used and/or (b) the volume ratio of microvoids in the polymer to said polymer and/or (c) the solubility of the insect attractant in the polymer on solidification. The proportion of insect attractant can in many instances go up to 45% by weight or even higher.

Thus, the proportion of insect attractant to resin can vary from small but effective amounts on the order of about 1% to the weight of the resin body up to about 45% by weight of the resin body. In general, it is preferred to use between about 5% up to about 30% based on the weight of resin body of the insect attractant. This is an optimum amount balancing the proportion of insect attractant against the time period over which the article emits the insect attractant and against the tendency of the insect attractant to "oil out". This "oiling out" is specifically avoided as a result of the use of foaming agent.

As stated, supra, various polymers are useful in the practice of our invention. Specific examples of polymers useful in the practice of our invention are as follows:
(a) DYLAN ® brand of low density polyethylene DYLAN ® is a trademark owned by the Atlantic Richfield Company of Los Angeles, Calif.;
(b) DYLITE ® of expandable polystyrene compositions. DYLITE ® is a trademark of the Atlantic Richfield Company of Los Angeles, Calif.;
(c) SUPER DYLAN ® a high density polyethylene. SUPER DYLAN ® is a trademark of the Atlantic Richfield Company of Los Angeles, Calif.;

(d) Blended polyethylene and carbon black as specifically taught in U.S. Pat. No. 4,369,267 issued on Jan. 18, 1983, the specification for which is incorporated by reference herein;

(e) Polystyrene as disclosed in U.S. Pat. No. 4,369,227 issued on Jan. 18, 1983, the specification for which is incorporated herein;

(f) Polyene/alpha-olefin as exemplified and disclosed in U.S. Pat. No. 4,369,291, the specification for which is incorporated by reference herein;

(g) Poly-alpha-olefins as exemplified in Canadian Letters Pat. No. 1,137,069 issued on Dec. 7, 1982, the specification for which is incorporated herein;

(h) Polymeric compositions as disclosed in Canadian Letters Pat. No. 1,137,068 issued on Dec. 7, 1982, the specification for which is incorporated by reference herein;

(i) Poly-alpha-olefins disclosed in Canadian Letters Pat. No. 1,137,067, the specification for which is incorporated by reference herein;

(j) Polyolefins described in Canadian Letters Pat. No. 1,137,066, the specification for which is incorporated by reference herein;

(k) Polyethylene oxides as disclosed in Canadian Letters Pat. No. 1,137,065 issued on Dec. 7, 1982, the specification for which is incorporated by reference herein;

(l) Olefin polymers and co-polymers as disclosed in Canadian Letters Pat. No. 1,139,737, the disclosure of which is incorporated by reference herein. Canadian Pat. No. 1,139,737 was issued on Jan. 18, 1983;

(m) Polyolefins disclosed in Canadian Letters Pat. No. 1,139,738, the disclosure of which is incorporated by reference herein. Canadian Pat. No. 1,139,738 was issued on Jan. 18, 1983;

(n) Chlorinated PVC as disclosed in *Polymer* 1982, 23 (7, Suppl.), 1051–6 abstracted at Chem. Abstracts 97: 145570y, 1982;

(o) Polyepsilon caprolactone co-polymers made by means of alcohol initiated polymerization as disclosed in *J. Polym. Sci. Polym. Chem. Ed.* 1982, 20(2), pages 319–26, abstracted at Chem. Abstracts, Volume 96: 123625x, 1982;

(p) Styrene acrylonitrile co-polymers as disclosed in Diss. Abstracts, Int. B, 1982, 42(8), 3346 and abstracted at Chem. Abstracts 96: 143750n (1982);

(q) Co-polymers of epsilon caprolactone with 1,4-butane diol as disclosed at Kauch. Rezine, 1982, (2), 8–9, abstracted at Chem. Abstracts, Volume 96: 182506g (1982);

(r) Polyesters as disclosed in U.S. Pat. No. 4,326,010, the specification for which is incorporated by reference herein;

(s) Chlorinated polyethylene as disclosed by Belorgey, et al, *J. Polym. Sci. Polym. Phys. Ed.* 1982, 20(2), 191–203;

(t) Plasticized polyepsilon caprolactone co-polymers containing dimethyl phthalate plasticizers as set forth in Japanese Pat. No. J81/147844, abstracted at Chem. Abstracts, Volume 96: 69984y (1982), the specification for which is incorporated by reference herein;

(u) Maleic anhydride modified adducts of polyepsilon caprolactone polyols and ethylenically unsaturated monomer as disclosed in U.S. Pat. No. 4,137,279 issued on Jan. 30, 1979, the specification for which is incorporated by reference herein;

(v) Polyurethane polymers having lactone backbones as disclosed in U.S. Pat. No. 4,156,067 issued on May 22, 1979, the disclosure of which is incorporated by reference herein;

(w) Polyurethane polyether resins wherein the resin is obtaied by reacting a polyfunctional lactone with a long chain polyalkylene diol and a urethane precursor as disclosed in U.S. Pat. No. 4,355,550 issued on Mar. 10, 1981, the disclosure of which is incorporated by reference herein; and (x) Resins having polyurethane backbones as disclosed in U.S. Pat. No. 3,975,350 issued on Aug. 17, 1976, the disclosure of which is incorporated by reference herein.

Optionally, downstream from the addition point of the insect attractant a gaseous or liquid containing blowing agent may be added (e.g., at barrel segments S-5, S-6, S-7, S-8 or S-9 and S-10) using the polymer addition barrel segment as a reference barrel segment "S-1". Examples of gaseous blowing agents are carbon dioxide, nitrogen, mixtures of nitrogen and carbon dioxide in proportions of from 1 up to 99% by volume nitrogen and 99 down to 1% by volume carbon dioxide, helium, mixtures of helium and nitrogen, mixtures of helium and carbon dioxide and other gaseous which are inert at the temperature and pressure of the polymer at the time of the extrusion operation. Thus, gas containing oxygen or other reactive gases, e.g., hydrogen, should be avoided. The pressure of the gas blowing agent being added to the extruder at the point of addition may vary from about 80 up to about 150 psig. Higher pressures may be used without adversely affecting the usefulness of the foamed insect attractant-containing polymer particle.

The feed rate change of insect attractant may be between about 0.5% up to about 45% by weight of the polymer.

The die of the extruder may create rod, sheet, film or ribbon. The resulting product may then, if desired, be pelletized to form foamed insect attractant-containing polymer particles or the ribbon may be used "as-is" as an insect attractant-containing polymeric article of manufacture itself.

In addition to the optional gaseous blowing agents (which are necessarily "insert" gases), blowing agents may be added at some point on the extruder which will create gaseous voids in the insect attractant-containing polymeric articles of our invention and these "blowing agents" are well known to one having ordinary skill in the art. Examples of such non-gaseous containing materials which yield gases on admixture with the polymer in the extruder but which are still inert to the insect attractant are as follows:

(i) Under high pressure, ethylene, methane, propane, butane, propylene, methyl chloride, methyl bromide, vinyl chloride and methylene dichloride as more specifically described in U.S. Pat. No. 2,387,730, the specification for which is incorporated by reference herein;

(ii) Ordinarily liquid material such as n-pentane, isopentane, cyclopentane, hexane and petroleum ester fractions or halogen hydrocarbons such as $CFCl_3$, $CF_2Cl_2$, $CH_3Cl$, $CH_2Cl_2$ separately or in admixture with one another as set forth in U.S. Pat. No. 3,758,425, column 4, lines 1–5, the specification for which is incorporated by reference herein;

(iii) Dichlorotetrafluoroethane, tetramethylmethane, monochlorodifluoromethane, dichlorodifluoromethane, and dichlorotetrafluoroethane as specifically described in U.S. Pat. Nos. 2,948,664 and 2,948,665 issued on Aug. 9, 1960, the specifications for which are incorporated herein by reference; and (iv) Azo bis(formamide); diazoaminobenzene; N,N'-dinitrosopentamethylene tetramine; N,N'-dimethyl-N,N'-dinitrosoterephthalamide; p,p'-oxy-bis(benzene sulfonyl semicarbazide); azo bis(isobutyronitrile); p,p'-oxy-bis(benzene sulfonyl hydrazide); p,p'-diphenyl-bis(sulfonyl hydrazide); benzene-sulfonyl hydrazide; m-benzene-bis(sulfonyl hydrazide) as more specifically described in U.S. Pat. No. 3,298,975 issued on Jan. 17, 1967, the specification for which is incorporated by reference herein.

The resulting extruded (and if desired pelletized) material may then be, for example, injection molded to form a useful article. Such injection molding can be carried out in accordance with the procedure as set forth in U.S. Pat. No. 3,268,636 issued on Aug. 23, 1966, the specification for which is incorporated by reference herein.

DETAILED DESCRIPTION OF THE DRAWINGS

Referring to FIGS. 1, 2, 3 and 4, FIGS. 3 and 4 shown in detail the ZOECON® sticky trap, more specifically a ZOECON PHEROCON®1C Trap (e.g., in FIG. 4 indicated by reference numeral 616a) and in FIG. 1 indicated by reference numerals 608c, 608d, 609a, 609b, 609c, 609d, 610a, 610c, 610d, 611a, 611c, 612a, 612c, 612d, 613a, 613c, 613d, 614a, 614b, 614c, 615a, 615c, 616a, 616b, 617a, 617b, 617c, 618a, 618b, 618c, 619c, 620a, 620b, 620c, 621a, 621b, 621c, 623a, 623b, 623c, 624a, 624b and 624c. The ZOECON PHEROCON®1C Trap has suspended in it as will be seen from FIGS. 3 and 4, a 2 cm×2 cm strip of slow release polymer (polyethylene) 6117 in FIGS. 3 and 4 containing insect attractant (N,N-diethyl-m-toluamide, the ethyl ester of 2-methyl-3-pentenoic acid, mixtures of N,N-diethyl-m-toluamide and the ethyl ester of 2-methyl-3-pentenoic acid or mixtures of N-N-diethyl-m-toluamide and dimethyl disulfide); or the 2 cm×2 cm strip contains the GOLDEN MALRIN® control.

The mixtures of N,N-diethyl-m-toluamide and the ethyl ester of 2-methyl-3-pentenoic acid may contain from 0.5% up to 99.5% of N,N-diethyl-m-toluamide and from 0.5% up to 99.5% of the ethyl ester of the ethyl ester of 2-methyl-3-pentenoic acid.

The mixtures of N,N-diethyl-m-toluamide and dimethyl disulfide may contain from 0.5% up to 99.5% of N,N-diethyl-m-toluamide and from 0.5% up to 99.5% of dimethyl disulfide, all percentages being weight percentages.

In addition, our invention contemplates the use of the mixtures containing three components; N,N-diethyl-m-toluamide, the ethyl ester of 2-methyl-3-pentenoic acid and dimethyl disulfide wherein each of the components may vary from 0.1% up to 99.9% with the other components being the remainder of the mixture.

The 2 cm×2 cm strip 6117 is suspended in the trap 616a from bar 6116 using holder 6118. Trap 616a has lower tray 6110 which will catch insect droppings or dead insects which do not adhere to the 2 cm×2 cm strip 6117. The lower tray 6110 is attached via strips 6112a and 6112b to upper holder 611 which is attached to suspension bar 6113 suspended by rod 6114 to the barn beam 6115 (in FIG. 2). The barn beam 6115 is held in a horizontal position by upright supports 602 and 606 (as will be seen in FIG. 2) which is firmly in place on the barn floor 6119. The 2 cm×2 cm strip 6117 is formulated in such apparatus as is set forth in FIG. 10 described in detail, infra. The traps containing the insect attractant, e.g, N,N-diethyl-m-toluamide, the ethyl ester of 2-methyl-3-pentenoic acid, mixtures of N,N-diethyl-m-toluamide and 2-methyl-3-pentenoic acid ethyl ester and mixtures of N,N-diethyl-m-toluamide and dimethyl disulfide and mixtures of N,N-diethyl-m-toluamide, 2-methyl-3-pentenoic acid ethyl ester and dimethyl disulfide or the GOLDEN MALRIN® control are placed in the goat barn having fencing panels 601 and 603 and inner support 604 and 605, an observation post 622 and experimental locations 608, 609, 610, 611, 612, 613, 614, 615, 616, 617, 618, 619, 620, 621, 623 and 624 has suspended in it the several Zoecon Pherocon 1C Traps each containing 2 cm×2 cm strips of formulated slow release insect attractants. Trap placement was replicated in four quadrants of the barn. Traps 616a, 616b, 615a, 615c and other traps were placed in the barn for seven days and the insects collected were identified and counted. Evidence of various insects visiting the traps were also counted, as fly specks inside or outside to the traps. All the test materials were compared with a standardized check treatment consisting of 0.5 grams of GOLDEN MALRIN® fly bait inside slow release packets hung like the other compounds as in strip 6117 in FIGS. 3 and 4.

FIGS. 5, 6, 7, 8 and 9 indicate the results of field trial tests using the apparatus set forth in FIGS. 1, 2, 3 and 4.

Figure 5:
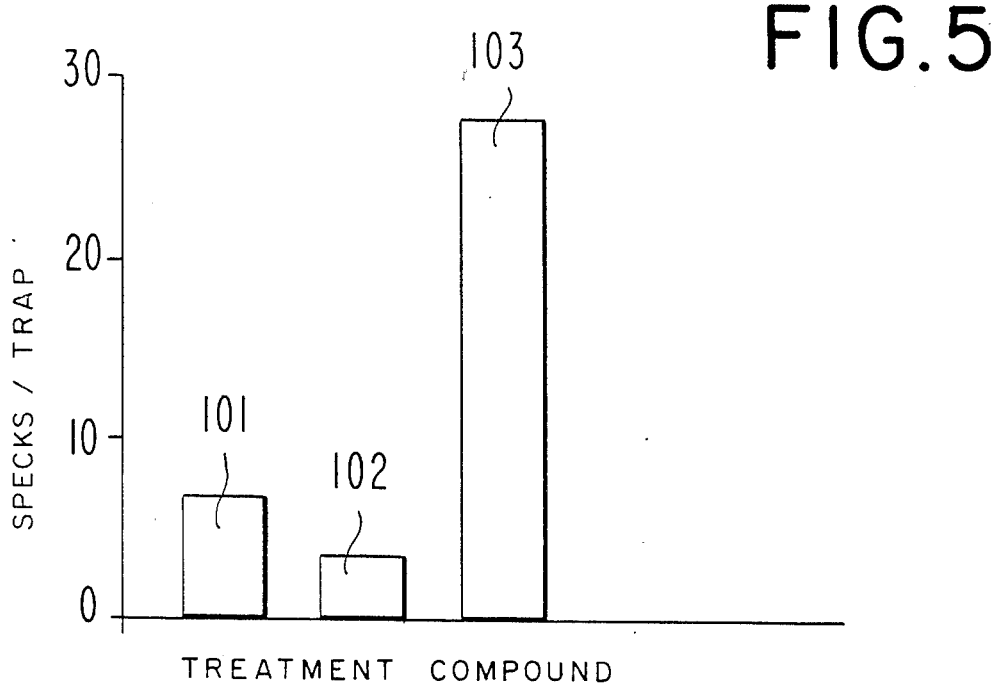
FIG. 5 is a bar graph showing a comparison of the field trial tests of attractants for house flies (*Musca domestica L.*(Diptera:Muscidae)) comparing n,n-diethyl-m-toluamide, the ethyl ester of N,N-diethyl-m-toluamide, the ethyl ester of the ethyl ester of 2-methyl-3-pentenoic acid and GOLDEN MALRIN ®, a mixture of (Z)-9-tricosene and methomyl which is methomyl(s-methyl N-[methyl-carbamoyl]oxy)thioacetimidate, the graph being compound vs. house flies per trap.

FIG. 5 is a series of bar graphs for field trial tests of the attractants N,N-diethyl-m-toluamide and the ethyl ester of 2-methyl-3-pentenoic acid and GOLDEN MALRIN® for house fly counts, inside the traps indicated by reference numeral 6117. Thus, the bar graph indicated by reference numeral 103 is the bar graph for N,N-diethyl-m-toluamide insofar as it attracts *Musca domestica L.*(Diptera:Muscidae) inside of such traps as trap 616a in FIGS. 3 and 4, the house flies being located on tray 6110 in FIGS. 3 and 4. Tray 6110 is also shown in FIG. 2. The bar graph indicated by reference numeral 102 is the bar graph for the ethyl ester of 2-methyl-3-pentenoic acid insofar as it attracts *Musca domestica L.*(Diptera:Muscidae). The bar graph indiated by reference numeral 101 is the bar graph for GOLDEN MALRIN® (insofar as it attracts *Musca domestica L.*(Diptera:Muscidae)). As stated, supra, FIG. 5 is a graph of flies/trap vs compound. Thus, the N,N-diethyl-m-toluamide in FIG. 5 gives rise to an attractancy of *Musca domestica L.*(Diptera:Muscidae) of 28.33 fly/trap; the ethyl ester of 2-methyl-3-pentenoic acid gives rise to an attractancy of 3.50 house fly/trap; and the GOLDEN MALRIN® gives rises to 6.75 house flies per trap.

Figure 6:
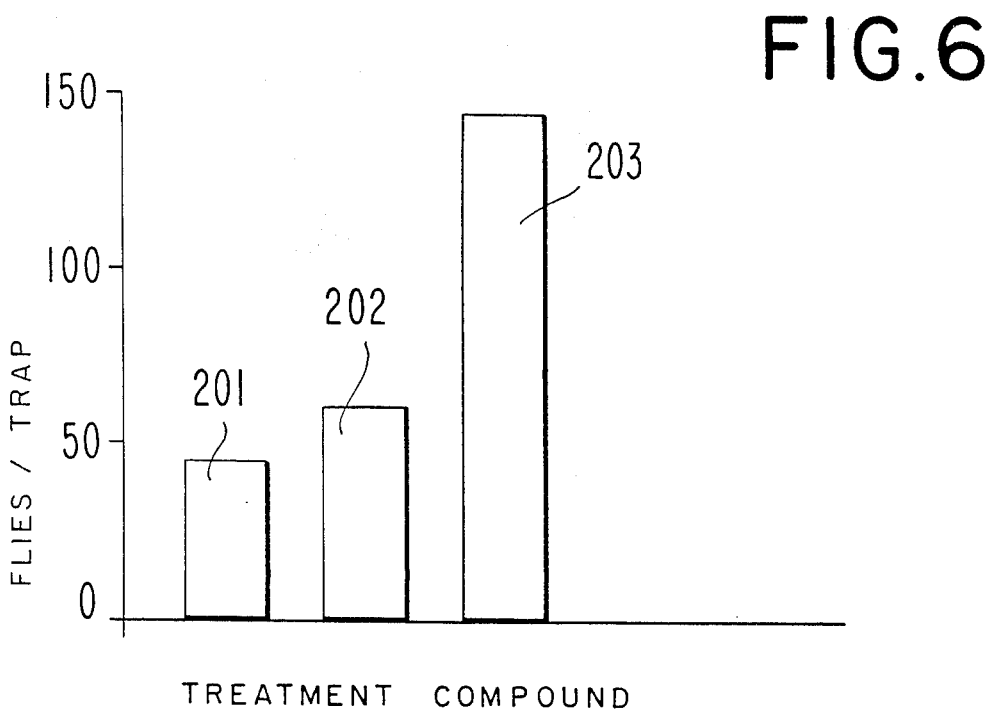
FIG. 6 is a bar graph showing a comparison of the field trial tests of attractants for house flies (*Musca domestica L.*(Diptera:Muscidae)) comparing N,N-diethyl-m-toluamide, the ethyl ester of the ethyl ester of 2-methyl-3-pentenoic acid and GOLDEN MALRIN ®, the graph being compound vs. house fly specks per trap, the house fly specks being located inside of the trap.

FIG. 6 is a series of bar graphs for field trial tests of the attractants N,N-diethyl-m-toluamide and the ethyl ester of 2-methyl-3-pentenoic acid and GOLDEN MALRIN® for house fly speck counts inside the traps indicated by reference numeral 6117. Thus, the bar graph indicated by reference numeral 203 is the bar graph for N,N-diethyl-m-toluamide insofar as it attracts (*Musca domestica L.*(Diptera:Muscidae) inside of such traps as trap 616a in FIGS. 3 and 4, the house fly specks being located on tray 6110 in FIGS. 3 and 4. Tray 6110 is also shown in FIG. 2. The bar graph indicated by reference numeral 202 is the bar graph for the ethyl ester of 2-methyl-3-pentenoic acid insofar as it attracts (*Musca domestica L.*(Diptera:Muscidae). The bar graph indicated by reference numeral 201 is the bar graph for GOLDEN MALRIN® (insofar as it attracts (*Musca*

*domestica L.*(Diptera:Muscidae)). As stated supra, FIG. 6 is a graph of fly speck/trap vs. compound. Thus, the N,N-diethyl-m-toluamide in FIG. 6 gives rise to an attractancy of (*Musca domestica L.*(Diptera:Muscidae) of 144.00 fly speck/trap; the ethyl ester of 2-methyl-3-pentenoic acid gives rise to an attractancy of 60.25 fly speck/trap and the GOLDEN MALRIN ® gives rise to 44.00 fly specks per trap.

Figure 7:
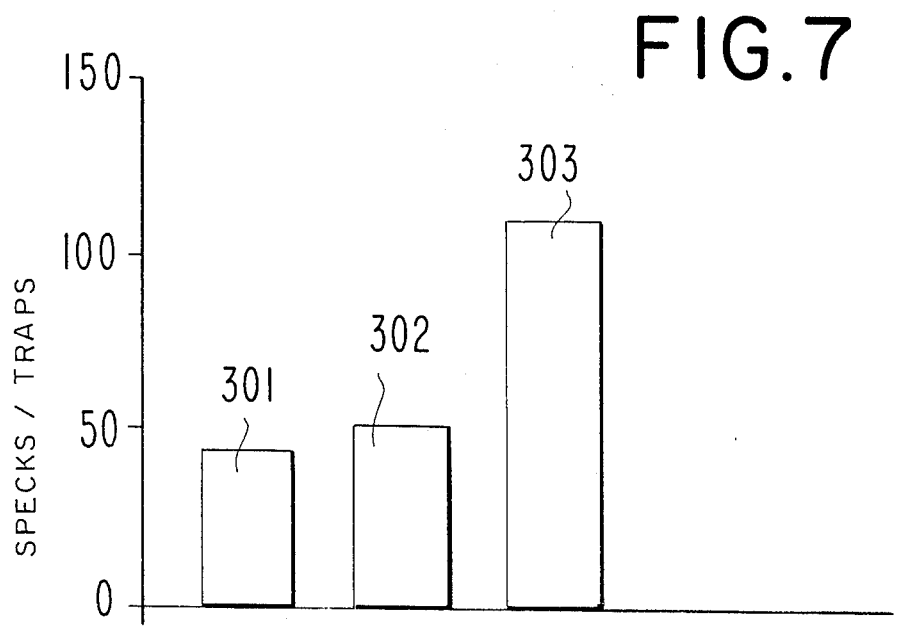
FIG. 7 is a bar graph showing a comparison of the field trial tests of attractants for house flies (*Musca domestica L.* (Diptera:Muscidae)) comparing N,N-diethyl-m-toluamide, the ethyl ester of the ethyl ester of 2-methyl-3-pentenoic acid and GOLDEN MALRIN ®, the graph being compound vs. house fly specks per trap, the house fly specks being outside of the traps.

FIG. 7 is a series of bar graphs for field trial tests of the attractants N,N-diethyl-m-toluamide, 2-methyl-3-pentenoic acid ethyl ester and GOLDEN MALRIN ® for house fly speck counts outside the traps indicated by reference numeral 6117. Thus, the bar graph indicated by reference numeral 303 is the bar graph for N,N-diethyl-m-toluamide insofar as it attracts (*Musca domestica L.*(Diptera:Muscidae) outside of such traps as trap 616a in FIGS. 3 and 4, the house fly specks being located outside of tray 6110 in FIGS. 3 and 4. Tray 6110 is also shown in FIG. 2. The bar graph indicated by reference numeral 302 is the bar graph for the ethyl ester of 2-methyl-3-pentenoic acid insofar as it attracts (*Musca domestica L.*(Diptera:Muscidae). The bar graph indicated by reference numeral 301 is the bar graph for GOLDEN MALRIN ® (insofar as it attracts (*Musca domestica L.*(Diptera:Muscidae)). As stated, supra, FIG. 7 is a graph of fly speck/trap vs. compound for the fly specks outside of the trap. Thus, the N,N-diethyl-m-toluamide in FIG. 7 gives rise to an attractancy of (*Musca domestica L.*(Diptera:Muscidae) of 109.333 fly speck/trap; the ethyl ester of 2-methyl-3-pentenoic acid gives rise to an attractancy of 51.00 fly speck/trap and the GOLDEN MALRIN ® gives rise to 42.25 gly speck/trap.

Figure 8:
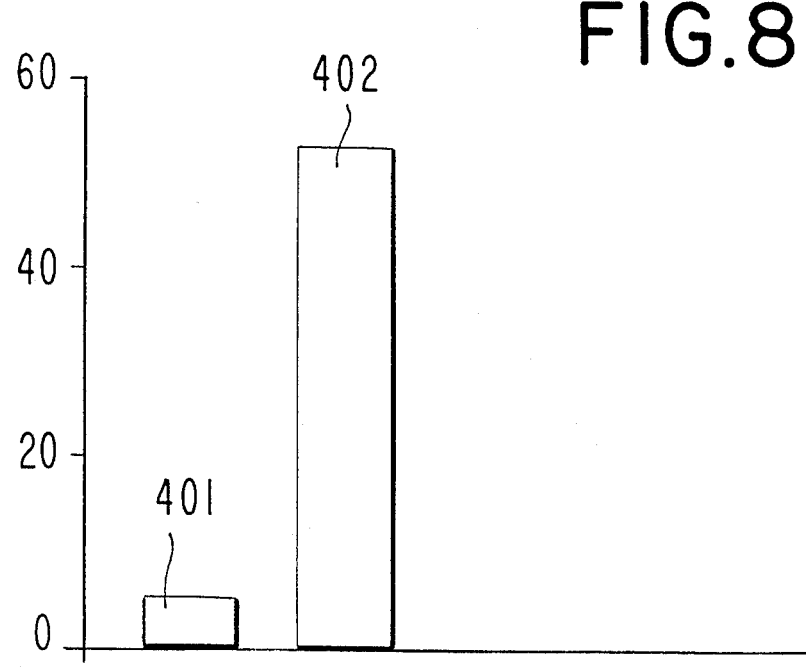
FIG. 8 is a bar graph showing a comparison of the field trial tests of attractants for house flies (*Musca domestica L.*(Diptera:Muscidae)) comparing a mixture (50:50 weight:weight) of N,N-diethyl-m-toluamide and the ethyl ester of 2-methyl-3-pentenoic acid and GOLDEN MALRIN ®, the graph being compound vs. house fly specks per trap, the house fly specks being located within the trap.

FIG. 8 is a series of bar graphs for field trial tests of the attractant, the mixture (50:50 weight:weight) of N,N-diethyl-m-toluamide and the ethyl ester of 2-methyl-3-pentenoic acid as well as for GOLDEN MALRIN ® for house fly speck counts inside the traps indicated by reference numeral 6117. Thus, the bar graph indicated by reference numeral 402 is the bar graph for the 50:50 weight:weight mixture of N,N-diethyl-m-toluamide and the ethyl ester of 2-methyl-3-pentenoic acid (insofar as the mixture attracts (*Musca domestica L.*(Diptera:Muscidae)) inside of such traps as trap 616a in FIGS. 3 and 4, the house fly specks being located on tray 610 in FIGS. 3 and 4. Tray 610 is also shown in FIG. 2. The bar graph indicated by reference numeral 401 is the bar graph for GOLDEN MALRIN ® (insofar as it attracts (*Musca domestica L*(Diptera:Muscidae)). As stated, supra, FIG. 8 is a graph of fly speck/trap vs. compound. Thus, the mixture of N,N-diethyl-m-toluamide and the ethyl ester of 2-methyl-3-pentenoic acid gives rise to an attractancy of (*Musca domestica L.*(Diptera:Muscidae) of 53.6 fly specks per trap; and the GOLDEN MALRIN ® gives rise to only 6.2 fly specks per trap.

Figure 9:
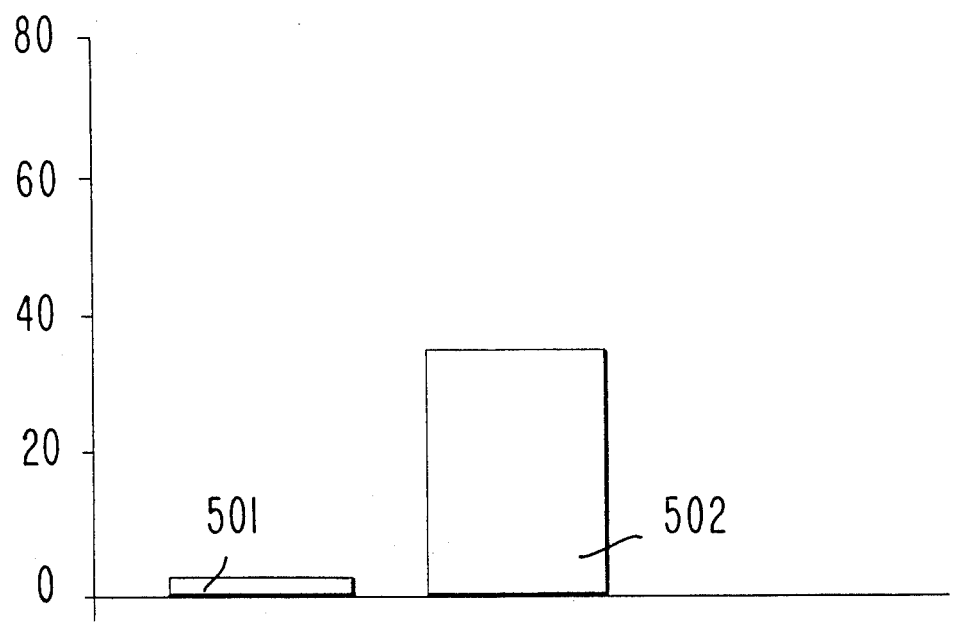
FIG. 9 is a bar graph showing a comparison of the field trial tests of attractants for house flies (*Musca domestica L*(Diptera:Muscidae)) comparing a mixture (50:50 weight:weight) of N,N-diethyl-m-toluamide and dimethyl disulfide, and GOLDEN MALRIN ®, the graph being a mixture of compounds vs. house fly specks per trap within the trap.

FIG. 9 is a series of bar graphs for field trial tests of the attractant which is the mixture (50:50 weight:weight) of N,N-diethyl-m-toluamide and dimethyl disulfide as well as for GOLDEN MALRIN ® for house speck counts inside the traps indicated by reference numeral 6117. Thus, the bar graph indicated by reference numeral 502 is the bar graph for the mixture of N,N-dimethyl-m-toluamide and dimethyl disulfide insofar as it attracts (*Musca domestica L.*(Diptera:Muscidae) inside of such traps as trap 616a in FIGS. 3 and 4, the house fly specks being located on tray 6110 in FIGS. 3 and 4. Tray 6110 is also shown in FIG. 2. The bar graph indicated by reference numeral 501 is the bar graph for GOLDEN MALRIN ® (insofar as it attracts (*Musca domestica L.*(Diptera:Muscidae)). As stated, supra, FIG. 9 is a graph of fly speck/trap vs. compound. Thus, the mixture of N,N-diethyl-m-toluamide and dimethyl disulfide in FIG. 9 gives rise to an attractancy of (*Musca domestica L.*(Diptera:Muscidae) of 35.40 fly speck/trap and the GOLDEN MALRIN ® gives rise to only 2.40 fly speck/trap.

Figure 10:
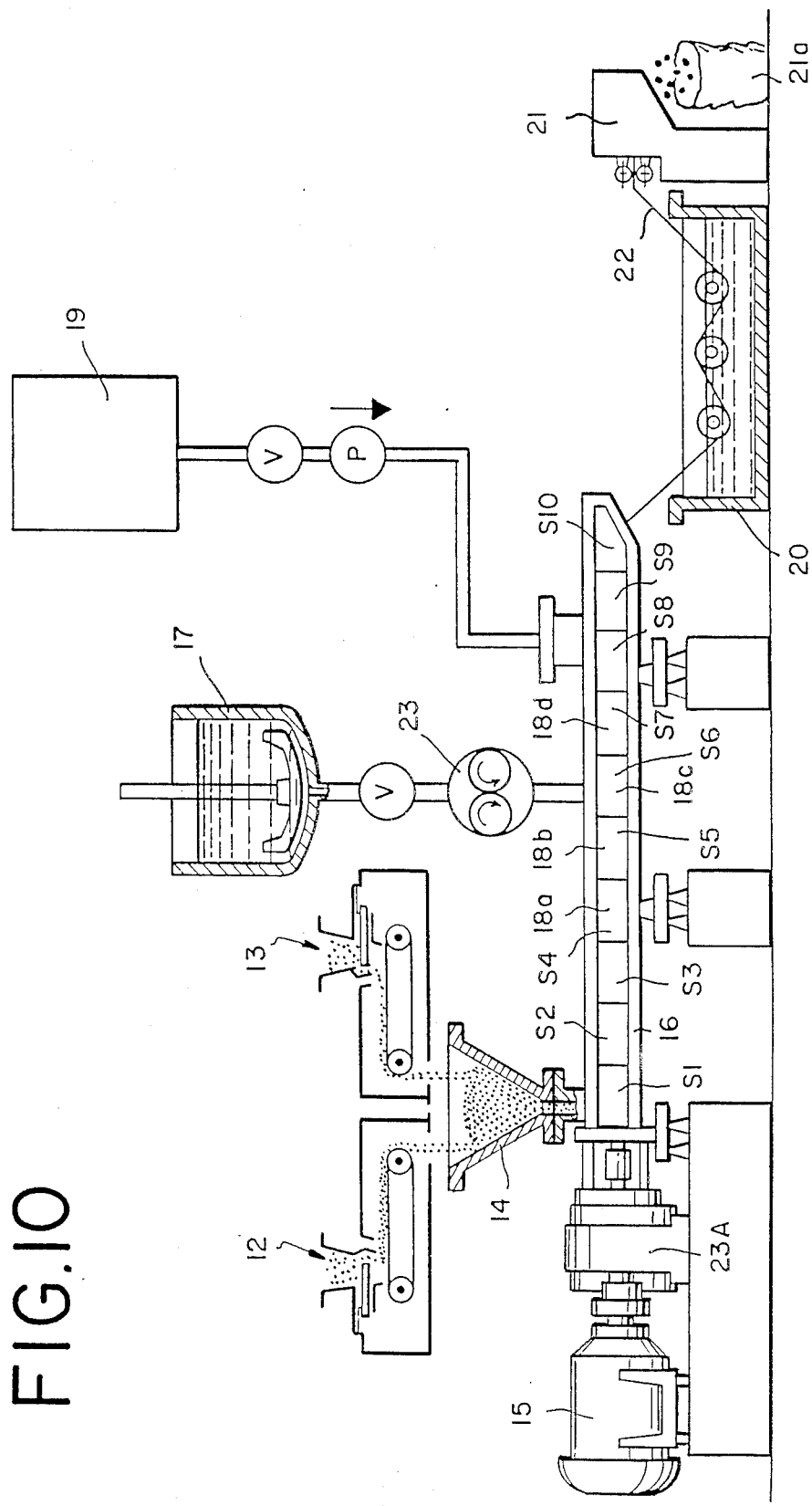
FIG. 10 is a cut-away side elevation schematic diagram of a screw extruder during the compounding of a resin with the insect attractants, N,N-diethyl-m-toluamide, the ethyl ester of 2-methyl-3-pentenoic acid, mixtures of same, as well as the mixtures of N,N-ethyl-m-toluamide and dimethyl disulfide, while simultaneously adding foaming agent into the hollow portion of the barrel of the extruder and incorporates the pelletizing apparatus used in pelletizing the extruded foamed tow product produced as a result of the extrusion operation.

FIG. 10 is a schematic cut-away elevation diagram of an extrusion and pelletizing apparatus useful in carrying out a process of our invention during the operation of said apparatus whereby the insect attractant is incorporated into a polymer such as a polyethylene. Motor 15 drives the extruder screws located at 23A in barrel 16, the extruder being operated at temperatures in the range of about 150° C. up to about 250° C. At the beginning of the barrel resin at source 12 together with additives, e.g., processing aids and densifiers at location 13 is added via addition funnel 14 into the extruder. Simultaneously (when the operation reaches "steady state"), insect attractants, N,N-diethyl-m-toluamide, the ethyl ester of 2-methyl-3-pentenoic acid, mixtures of N,N-diethyl-m-toluamide and the ethyl ester of 2-methyl-3-pentenoic acid and, mixtures of N,N-diethyl-m-toluamide and dimethyl disulfide and mixtures of N,N-diethyl-m-toluamide, the ethyl ester of 2-methyl-3-pentenoic acid and dimethyl disulfide is added to the extruder at 1, 2 or more of barrel segments S-3, S-4, S-5, S-6, S-7 and S-8 of the extruder (which may be a twin screw or single screw extruder) at locations 18a, 18b, 18c and 18d (for example) by means of gear pump 23 from source 17. For source 19 into barrel segments S-5, S-6, S-7, S-8, S-9 and S-10, a gaseous or liquid blowing agent, e.g., nitrogen, carbon dioxide and the like as described, supra, are added simultaneously with the addition of the insect attractant, e.g., N,N-diethyl-m-toluamide, the ethyl ester of 2-methyl-3-pentenoic acid, mixtures of same, the mixtures of N,N-diethyl-m-toluamide and dimethyl disulfide or mixtures of N,N-diethyl-m-toluamide, the the ethyl ester of 2-methyl-3-pentenoic acid and dimethyl disulfide. The feed rate range of resin is about 80-300 pounds per hour. The feed rate range of the insect attractant is between 1 and 35% of the feed rate range of the resin. The blowing agent range is such that the pressure of the gas or the pressure over the liquid being fed into the extruder is between about 50 and 200 psig if, indeed, blowing agent is added. If desired, the extruded ribbon or cylinder may be passed through water bath 20 and pelletized in pelletizer 21 and then passed into collection apparatus 21a.

It is well known that the N,N-diethyl-m-toluamide is an insect repellent as is set forth in Published Japanese Application No. J84/042646 (which discloses an insect repellent composition containing as active constituents N,N-diethyl-m-toluamide and halobenzoylpropionic acid esters abstracted as follows:

---

BADI         D21        77-05578Y/04 = J8 4042-646-B
Synergistic insect repellent compsns. - of diethyl toluamide and alkyl halobenzoyl propionates
   BASF AG 05.07.75-DE-530070
   B05 (16.10.84) *BE-843684-A A01n-37/42
22.06.76 as 072844(288RH)
Insect repellent compsn. are new contg. as active constituents N,N—dimethyl-toluamide and a halobenzoylpropionic acid ester of formula (A) In (A) X is halo; R is 1–4 C alkyl opt. substd. by Cl or —OMe. Specifically claimed is ethyl beta-(4-bromobenzoyl) propionate.

-continued

The effectiveness of the toluamide against mosquitos is combined with that of (A) against houseflies, and a synergistic effect is shown.
A preferred insect repellent compsn. is a mixt. of N,N—diethyl-rh-toluamide (II) and ethyl beta-(4-bromobenzoyl) propionate (I), esp. in ratio of 6:1 to 1:6 (J52010419-A).(4pp)

N,N-diethyl-m-toluamide is also known as a cockroach and mosquito repellent as set forth in Chemical Business, September 1985, at page 45, to wit:

Roach Offender

If you've seen cockroaches where we've seen cockroaches, you probably think that nothing turns away these hardy insects. Researches at the Department of Agriculture's Gainesville, FL, laboratory, however, say that some chemical cousins of the well-known mosquito-chaser DEET effectively discourage German roaches. USDA is now seeking patents on the compounds, said to keep roaches out of such favorite breeding spots as boxes and cracks for a month or more.

N,N-diethyl-m-toluamide is also known as a female Pink Bollworm Moth attractant as set forth in Science, Jan. 5, 1968 issue (by D. S. Greenberg, at pages 99 and 100) and also as set forth by Neumark, et al, Environmental Letters 7(1), 21-30 (1974) abstracted at Chemical Abstracts, Volume 81, 1974, Abstract No. 14689c.

Thus, the attractancy determined in the instant invention for N,N-diethyl-m-toluamide is surprising and unexpected. However, it has now been determined that the N,N-diethyl-m-toluamide is an attractant for *Musca domestica L.*(Diptera:Muscidae) in the air stream (at relatively low concentrations) and still acts as a *repellent* when coated on an object, e.g., the human epidermis. Thus, N,N-diethyl-m-toluamide can be used both as an attract and a repellent depending upon the concentrations used.

The concentrations of all materials tested herein are at the level of 5% in polymer.

It is noteworthy tht dimethyl disulfide has heretofore been discovered alone as a mosquito attractant (culicidae) but its use in conjunction with N,N-diethyl-m-toluamide is unknown. Thus, U.S. Pat. Ser. No. 901,647 filed on Aug. 29, 1986 discloses the use of dimethyl disulfide as a mosquito attractant when taken alone or in combination with dibutylsuccinate.

The ethyl ester of 2-methyl-3-pentenoic acid may be prepared according to the procedure as set forth in U.S. Pat. No. 4,000,327 issued on Dec. 28, 1976 at Example XL or at Example II. U.S. Pat. No. 4,000,327 issued on Dec. 28, 1986 is incorporated herein by reference. That patent discloses the use in berry fruit flavors of the the ethyl ester of 2-methyl-3-pentenoic acid.

What is claimed is:

1. A method of attracting *Musca domestica L.*(Diptera:Muscidae) to an insect trap comprising the step of exposing the environment surrounding said trap to an insect attractant-containing polymer which consists of a mixture of a polymer and from about 1% up to about 45% by weight of said polymer of the ethyl ester of 2-methyl-3-pentenoic acid, said polymer being compatible with said ethyl ester of 2-methyl-3-pentenoic acid.

* * * * *